United States Patent [19]

Bick

[11] Patent Number: 5,151,080
[45] Date of Patent: Sep. 29, 1992

[54] METHOD AND APPARATUS FOR INDUCING AND ESTABLISHING A CHANGED STATE OF CONSCIOUSNESS

[76] Inventor: Claus Bick, Felsenland-Bick-Klinik, D-6783 Dahn, Fed. Rep. of Germany

[21] Appl. No.: 490,552
[22] PCT Filed: Aug. 28, 1990
[86] PCT No.: PCT/CH89/00153
§ 371 Date: Apr. 27, 1990
§ 102(e) Date: Apr. 24, 1990
[87] PCT Pub. No.: WO90/01967
PCT Pub. Date: Mar. 8, 1990

[30] Foreign Application Priority Data

Aug. 30, 1988 [CH] Switzerland ............ 3219/88

[51] Int. Cl.⁵ ............................................. A61M 21/00
[52] U.S. Cl. ........................................ 600/28; 600/26
[58] Field of Search ............... 600/26, 27, 28; 381/54, 381/73.1, 61

[56] References Cited

U.S. PATENT DOCUMENTS

| | | | |
|---|---|---|---|
| 2,943,152 | 6/1960 | Licklinder | 381/54 |
| 3,712,292 | 1/1973 | Zentmeyer | 600/28 |
| 3,884,218 | 5/1975 | Monroe | 600/28 |
| 4,082,918 | 4/1978 | Chang | 600/28 |
| 4,717,343 | 1/1988 | Densky . | |

FOREIGN PATENT DOCUMENTS 3628420 2/1988 Fed. Rep. of Germany .
2124490 2/1984 United Kingdom .

Primary Examiner—William E. Kamm
Assistant Examiner—Scott R. Akers
Attorney, Agent, or Firm—Spencer, Frank & Schneider

[57] ABSTRACT

An electroacoustic device includes a sound generator as well as a system for producing synthetic human speech, connected to a modulation stage for superimposing the output signals thereof. The superimposed output signals are applied via an amplifier stage to one of a headphone system or loudspeaker system.

2 Claims, 1 Drawing Sheet

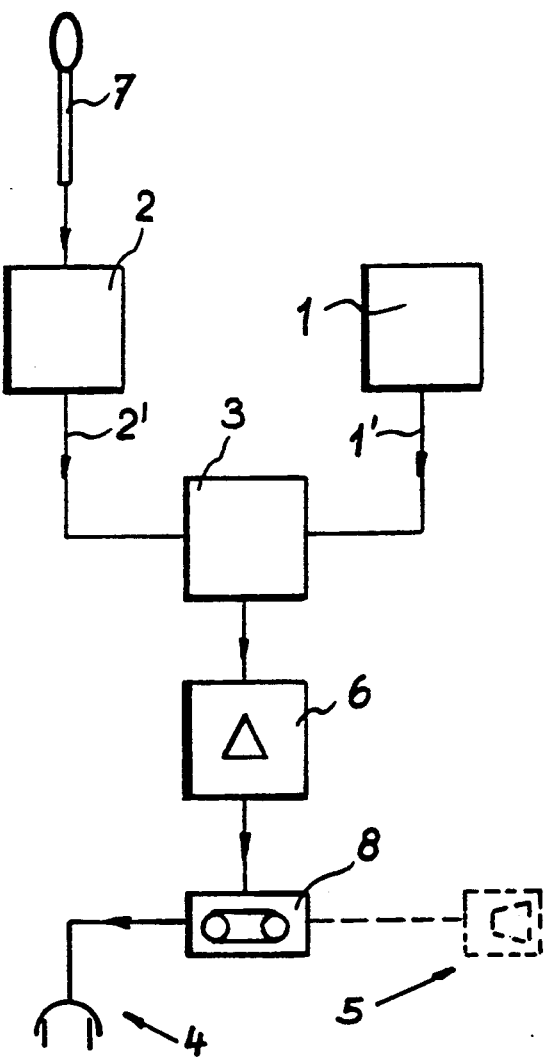

5,151,080

METHOD AND APPARATUS FOR INDUCING AND ESTABLISHING A CHANGED STATE OF CONSCIOUSNESS

BACKGROUND OF THE INVENTION

1. Field of the Invention

The present invention relates to a method and apparatus for inducing and establishing a deepened state of in a human that is physically and psychically (hypnotically) relaxed or changed by employing electroacoustic means.

2. Background Information

Psychogenic-therapy methods in the form of suggestive treatment with therapeutic and prophylactic character are gaining more and more in importance because there exists a very high probability of positively influencing the subconscious mind. Through this treatment, carried out in a deepened physical and psychical (hypnotical) state of relaxation—which is in itself already of great therapeutic effect—negative mental (disturbing) factors, which are fixed in the subconscious mind and evoke (subconsciously) misguided behavior, are replaced suggestively by positive, mental-motivating elements.

In spite of the necessity of individual, different treatment for executing the aforementioned exchange, it is, in order to relieve the treating therapist, both unavoidable and possible to induce and establish at least the deepened state of consciousness that is physically and psychically (hypnotically) relaxed or changed by employing electroacoustic auxiliary means.

The applicant has already described an apparatus in this connection for carrying out hypnotherapy, with which the physician conducting the therapy is able to reach simultaneously via sound carrier or microphone several patients wearing headphones, and exercise a suggestive influence on them for inducing and deepening the hypnosis and for the subsequent return out of the hypnosis.

In this connection, it was pointed out that certain sounds, in particular the rushing of the sea, i.e., the crashing of waves, had a very high sedative effect. To be able to utilize this, the control part of the aforementioned apparatus is provided with a suitable sound generator in order to bring the rushing of the sea alone by itself as well as superimposed, on the headphones for group and individual suggestion.

It is true that all this does relieve the therapist as regards previous individual methods of induction, such as the fascination method and the fixation method, but the effectiveness on the individuals remains very different, which demands in the end no lesser expenditure of time.

In the meantime, however, the results of years of scientific research by the inventor have revealed possibilities of essentially accelerating and deepening the induction and establishment of a deepened state of consciousness that is physically and psychically relaxed or changed.

From the findings of the inventor, upon inducing the condition of hypnosis a sinking of the activity of the left (with right-handers) half of the brain (fatigue effect) takes place, i.e. a damping of understanding and sense; and the censor becomes inattentive due to threshold tiring or distraction; which, on the other hand, results in the restriction of the consciousness on the left side, as restriction of the control of the censors; the sinking of the brain activity on the left hemisphere means, hence, a kind of dazed feeling, sleepiness, even inattentiveness on the part of the censor (C. H. Bick, Hypnoanalyse, in Laux/Schubert, Klinische Hypnose, Centaurus-Verlagsgesellshaft, Pfafferweiler); the inventor has set himself the task of creating a method of the aforementioned kind which is suitable for accelerating and deepening the induction and establishment of the deepened physical and psychical state of relaxation in accordance with the foregoing findings.

SUMMARY OF THE INVENTION

This is achieved according to the invention in that the electromagnetic sound signal as well as the output signal of a system for producing synthetic human speech are conveyed, each other superimposed, to the human ear by way of headphones or loudspeakers.

In this connection, it is of advantage that the sound signals simulate the rushing of waves, upon which the speech signals are modulated into a form that is at least partially, no longer understandable.

Essentially, therefore, the rushing of the waves sound is in the foreground, out of which only rudimentary, incomprehensible or scarcely understandable words are audible. These seemingly nonsensical stimulation signals and word information lead, in the left half of the brain, hence, in the rational area, to a comparatively very fast, apparent tiring or switch-off process with, among other things, strongly reduced sense, logic and control, through which, in a kind of switching, the right half of the brain is now to a large degree receptive to suggestion.

Further, the present invention relates to an apparatus for executing the method, which distinguishes itself according to the invention in that the electroacoustic means for inducing and establishing a changed state of consciousness comprises a sound generator as well as a system for producing synthetic human speech, which are connected to a modulation stage disposed downstream for superimposing the output signals thereof; said output signals being applied via amplifier means to a headphone system or loudspeaker system.

In a preferred embodiment of the invention, the system for generating synthetic human speech is a vocoder for coding speech and producing a robot voice.

BRIEF DESCRIPTION OF THE DRAWING

The drawing shows a block diagram of an embodiment in accordance with the invention.

DETAILED DESCRIPTION OF A PREFERRED EMBODIMENT

An embodiment for executing the method according to the invention will now be described in more detail with reference to the accompanying block diagram.

The apparatus for inducing and establishing a deepened state of consciousness that is physically and psychically relaxed or changed shown in the block diagram comprises a sound generator 1, with the rushing of the sea, preferably swelling up-and-down, being generated on the output 1' thereof; as well as a vocoder 2, with speech, introduced via a microphone 7, appearing coded like an incomprehensible or scarcely understandable robot voice on the output 2' thereof.

Both outputs 1' and 2' are adjacent to a modulation stage 3, which permits the rushing of the sea and the robot voice to be superimposed; a superimposed output signal being capable of being fed via a preferably adjustable amplifier stage 6 to a headphone system 4 or a loudspeaker system 5 having one or more headphones or loudspeakers, respectively.

Preferably, a sound-recording and sound-reproduction unit 8 is inserted between amplifier stage 6 and playback systems 4 or 5, which permit both the superimposed output signal for inducing and establishing the hypnotic state as well as the subsequent, normally-spoken suggestive information, to be recorded, stored and played back, for instance by means of a recording tape as carrier means.

Recorder tapes produced in such manner can then be individually and repeatedly employed.

Also, the apparatus according to the invention can be developed as a multistage station.

Vocoder, sound generator, modulation stage and amplifier stage can also be combined into a compact apparatus.

The specified apparatus is suitable for essentially accelerating and deepening the induction and establishment of a deepened state of consciousness that is physically and psychically relaxed and changed by the seemingly nonsensical stimulation signals and word information that is fed to the ear, and leads in the left half of the brain to a comparatively very fast threshold tiring or switch-off process with, among other things, strongly reduced sense, logic and control, and the right half of the brain being thereby to a large degree receptive to suggestive information and instruction.

I claim:

1. A method for inducing and establishing a deepened state of consciousness in a human that is physically and psychically relaxed or changed by employing electro-acoustic means for creating and generating electromagnetic sound signals and for producing electronically altered and synthetic human speech signals, the method comprising:

generating said sound signals;

producing said synthetic human speech signals;

superimposing said sound signals and said synthetic human speech signals to produce a superimposed signal; and conveying said superimposed signal to the ears of a human by way of one of headphones and loudspeakers.

2. The method as defined in claim 1, wherein the sound signals comprise noise signals which simulate the sound of crashing waves and the superimposing is performed by modulating said synthetic human speech signals so that said synthetic human speech signals are, at least partially, scarcely understandable.

* * * * *

UNITED STATES PATENT AND TRADEMARK OFFICE
CERTIFICATE OF CORRECTION

PATENT NO.   : 5,151,080

DATED        : September 29, 1992

INVENTOR(S)  : Claus BICK

It is certified that error appears in the above-identified patent and that said Letters Patent is hereby corrected as shown below:

Title page:

Item [22] should be August 28, 1989; and

Item [86] the §102(e) date should be April 27, 1990.

Signed and Sealed this

Seventh Day of September, 1993

Attest:

BRUCE LEHMAN

Attesting Officer     Commissioner of Patents and Trademarks